US011234601B2

(12) United States Patent
Kaiser et al.

(10) Patent No.: US 11,234,601 B2
(45) Date of Patent: Feb. 1, 2022

(54) MULTISENSOR CARDIAC FUNCTION MONITORING AND ANALYTICS SYSTEMS

(71) Applicant: THE REGENTS OF THE UNIVERSITY OF CALIFORNIA, Oakland, CA (US)

(72) Inventors: William Kaiser, Los Angeles, CA (US); Nils Peter Borgstrom, Los Angeles, CA (US); Per Henrik Borgstrom, Charlestown, MA (US); Aman Mahajan, Sherman Oaks, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 179 days.

(21) Appl. No.: 16/101,383

(22) Filed: Aug. 10, 2018

(65) Prior Publication Data
US 2019/0059748 A1    Feb. 28, 2019

Related U.S. Application Data

(60) Provisional application No. 62/552,864, filed on Aug. 31, 2017.

(51) Int. Cl.
| *A61B 5/02* | (2006.01) |
| *A61B 7/04* | (2006.01) |
| *A61B 5/00* | (2006.01) |
| *A61B 7/02* | (2006.01) |
| *A61B 5/316* | (2021.01) |

(Continued)

(52) U.S. Cl.
CPC .......... *A61B 5/02028* (2013.01); *A61B 5/316* (2021.01); *A61B 5/352* (2021.01); *A61B 5/7203* (2013.01); *A61B 5/7267* (2013.01); *A61B 7/026* (2013.01); *A61B 7/04* (2013.01); *A61B 5/026* (2013.01); *A61B 5/6823* (2013.01); *A61B 5/6831* (2013.01); *A61B 2562/0204* (2013.01)

(58) Field of Classification Search
USPC ...................................... 600/528
See application file for complete search history.

(56) References Cited

U.S. PATENT DOCUMENTS

| 8,473,041 B2 | 6/2013 | Bartnik |
| 8,515,201 B1 | 8/2013 | Murray Herrera |

(Continued)

OTHER PUBLICATIONS

ISA/US, United States Patent and Trademark Office (USPTO), International Search Report and Written Opinion dated Oct. 19, 2018, related PCT international application No. PCT/US2018/046575, pp. 1-9, claims searched, pp. 10-13.

(Continued)

*Primary Examiner* — Nicole F Lavert
(74) *Attorney, Agent, or Firm* — O'Banion & Ritchey LLP; John P. O'Banion

(57) ABSTRACT

An Integrated CardioRespiratory (ICR) System is provided for continuous Ejection Fraction (EF) measurement using a wearable device comprising a plurality of acoustic sensors. The ICR system performs signal processing computations to characterize cardiac acoustic signals that are generated by cardiac hemodynamic flow, cardiac valve, and tissue motion, and may use advanced machine learning methods to provide accurate computation of EF.

23 Claims, 11 Drawing Sheets

(51) Int. Cl.
*A61B 5/352* (2021.01)
*A61B 5/026* (2006.01)

(56) References Cited

U.S. PATENT DOCUMENTS

| | | | |
|---|---|---|---|
| 10,959,629 | B2 | 3/2021 | Kaiser |
| 2003/0144702 | A1 | 7/2003 | Yu |
| 2003/0208240 | A1 | 11/2003 | Pastore |
| 2008/0001735 | A1 | 1/2008 | Tran |
| 2008/0154144 | A1 | 6/2008 | Unver |
| 2008/0167566 | A1 | 7/2008 | Unver |
| 2009/0030292 | A1 | 1/2009 | Bartnik |
| 2009/0209875 | A1 | 8/2009 | Giorgis |
| 2011/0152638 | A1 | 6/2011 | Bartnik |
| 2014/0094870 | A1 | 4/2014 | Renesto |
| 2016/0019914 | A1 | 1/2016 | Sugiyama |
| 2016/0175598 | A1* | 6/2016 | Volpe ............ A61N 1/046 607/4 |
| 2016/0270738 | A1* | 9/2016 | Volpe ............ A61B 7/003 |
| 2018/0160917 | A1 | 6/2018 | Liu |
| 2018/0168473 | A1 | 6/2018 | Du |
| 2019/0059747 | A1 | 2/2019 | Kaiser |
| 2019/0133516 | A1 | 5/2019 | Banet |
| 2020/0170527 | A1 | 6/2020 | Kale |

OTHER PUBLICATIONS

ISA/US, United States Patent and Trademark Office (USPTO), International Search Report and Written Opinion dated Oct. 24, 2018, related PCT international application No. PCT/US2018/046378, pp. 1-10, claims searched, pp. 11-16.

European Patent Office (EPO), extended European search report dated Apr. 19, 2021, related European patent application No. 18851186.9, pp. 1-11, claims searched, pp. 12-16.

Moyers, Brian et al., "Performance of Phonoelectrocardiographic Left Ventricular Systolic Time Intervals and B-Type Natriuretic Peptide Levels in the Diagnosis of Left Ventricular Dysfunction", A.N.E., Apr. 2007, vol. 12, No. 2, pp. 89-97.

Garrard, Clifford L, Jr. et al., "The Relationship of Alterations in Systolic Time Intervals to Ejection Fraction in Patients with Cardiac Disease", Circulation, vol. XLII, Sep. 1970, pp. 455-462.

Gill, D. et al., "Detection and Identification of Heart Sounds Using Homomorphic Envelogram and Self-Organizing Probabilistic Model", Computers in Cardiology, 2005: 32:957-960.

Yeh, Yun-Chi et al., "QRS complexes detection for ECG signal: The Difference Operation Method", Computer Methods and Programs in Biomedicine 91 (2008) 245-254.

Borgstrom, Nils Peter, UCLA Electronic Theses and Dissertations, "The Integrated CardioRespiratory Heart Function Monitoring System", 2017, 1 page, first published Oct. 12, 2019, declaration of publication date from ProQuest, pp. 2-5, dissertation, pp. 6-154.

European Patent Office (EPO), extended European search report dated Apr. 30, 2021, related European patent application No. 18851588.6, pp. 1-13, claims searched, pp. 14-18.

Saraf, Kanav et al., "Fully-Automated Diagnosis of Aortic Stenosis Using Phonocardiogram-Based Features", Annu Int Conf IEEE Eng Med Biol Soc. 2019, Jul. 2019.6673-6676.

Saraf, Kanav et al., "Assessment of Left Ventricular Diastolic Function using Phonocardiogram Signals: A Comparison with Echocardiography", Annu Int Conf IEEE Eng Med Biol Soc. 2020, Jul. 2020:4067-4070.

Eddleman, Jr, E. E. et al., "The use of the systolic time intervals for predicting left ventricular ejection fracion in ischemic heart disease", American Heart Journal, vol. 93, No. 4, Apr. 1977, pp. 450-454.

* cited by examiner

MULTISENSOR CARDIAC FUNCTION MONITORING AND ANALYTICS SYSTEMS

CROSS-REFERENCE TO RELATED APPLICATIONS

This application claims priority to, and the benefit of, U.S. provisional patent application Ser. No. 62/552,864 filed on Aug. 31, 2017, incorporated herein by reference in its entirety.

STATEMENT REGARDING FEDERALLY SPONSORED RESEARCH OR DEVELOPMENT

Not Applicable

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to patient monitoring, and more particularly to monitoring cardiac function.

2. Background Discussion

A critical need has emerged for heart function monitoring to enable constant vigilant monitoring of patients who are at risk due to Congestive Heart Failure (CHF). Over 5 million Americans suffer from CHF which accounts for over one in 9 deaths in the U.S. Acute worsening of cardiac function is one of the most common causes for admission to hospital treatment and the leading contributor to healthcare delivery cost. An urgent and unmet need exists for continuous, non-invasive monitoring of heart function that can reduce the burden of heart disease through identification of patients at risk and opportunity for early prevention and intervention of disease conditions. Past technology solutions have focused on monitoring only of the Electrocardiography (ECG) signal sources. However, the critical biomechanical function of the heart is not monitored, thus limiting the nature of the assessment.

Current methods for measuring EF include point in time assessment with advanced echocardiography technology and MRI systems along with methods including Radionuclide Ventriculography or Radionuclide Angiography. However, these methods are costly in application, require presence and support of expert technicians, and are not capable of continuous monitoring.

BRIEF SUMMARY

An important diagnostic indicator of CHF is the measurement of the critical reduction in the Left Ventricle Ejection Fraction (EF) heart function. The EF value is the fraction of volume of blood in the left ventricle that is delivered during each heartbeat. Low values of EF indicate a CHF condition presence and provide a data point required for determining patient care. Large decreases in EF indicate risk of mortality.

Accordingly, an aspect of the present technology is an Integrated CardioRespiratory (ICR) System that enables continuous EF measurement with a wearable device providing clinicians with the most critical assessment metric for patient care. In a preferred embodiment, the ICR system performs signal processing computations to characterize cardiac acoustic signals that are generated by cardiac hemodynamic flow, cardiac valve, and tissue motion. In another embodiment, signal processing is accompanied with advanced machine learning methods to provide accurate computation of EF.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

1. Introduction

An important diagnostic indicator of CHF is the measurement of the Left Ventricle Ejection Fraction (EF) heart function. The EF value is the fraction of volume of blood in the left ventricle that is delivered during each heartbeat. Low values of EF are indicative of a CHF condition and provide a data point required for determining patient care. Large decreases in EF indicate risk of mortality. This risk is not indicated by other measurements, including ECG, as these methods do not directly measure heart function.

The ICR system described herein enables continuous EF measurement with a wearable device providing clinicians with the most critical assessment metric for patient care. Specifically, the ICR system applies compact, wearable acoustic sensor devices and ECG sensor electrodes in a convenient patient belt or adhesive attachment application system. The ICR system performs signal processing computation to characterize heart sound signals that are generated by cardiac hemodynamic flow, cardiac valve, and tissue motion. Signal processing is accompanied with advanced machine learning methods to provide accurate computation of EF.

The ICR system beneficially provides clinical patient care via continuous and convenient monitoring, ensuring patient safety with benefits to patients and clinicians as well as hospital facilities that can advance fundamental care. The ICR system beneficially is also advantageous for outpatient treatment by providing cardiac function monitoring to patients who otherwise will not receive assessment. Finally, the ICR system beneficially is further advantageous in residential monitoring, providing an unprecedented heart function remote diagnostic capability enabling early intervention and advanced perioperative care delivery.

2. ICR System Components

Figure 1:
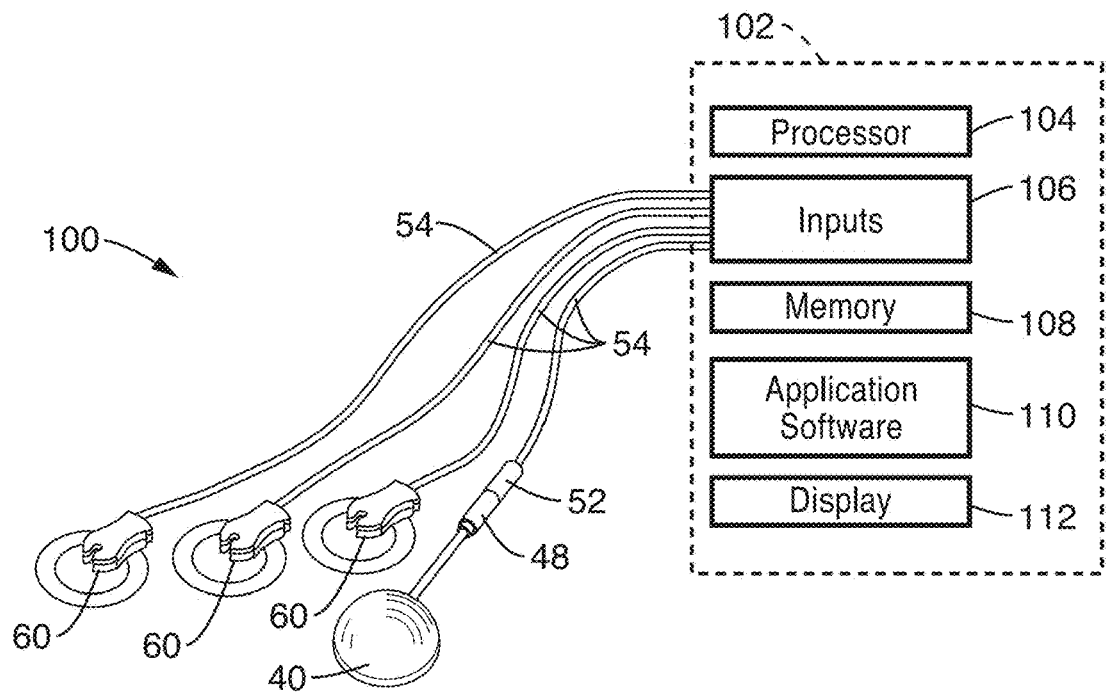
FIG. 1 shows a schematic diagram of the ICR monitoring system of the present description.

In a preferred embodiment illustrated in FIG. 1, the ICR monitoring system 100 generally employs the following components: ICR acoustic sensors 40, ECG sensor electrodes 60; and an ICR patient monitor 102. Monitor 102 comprises inputs 106 for receiving signals from ICR acoustic sensors 40 and ECG sensor electrodes 60 via leads 54. Application programming 110 is provided within memory 108 for analyzing data from ICR acoustic sensors 40 and ECG sensor electrodes 60 via execution on processor 104. Patient monitor 102 may also comprise a display 112 for outputting computed analysis results. It is appreciated that a simplified version of the system only incorporates ICR acoustic sensors (without the need of ECG sensors), in which the application programming is configured to analyze acoustic data via a PCG-gated segmentation scheme (described in further detail below).

Figure 2A:
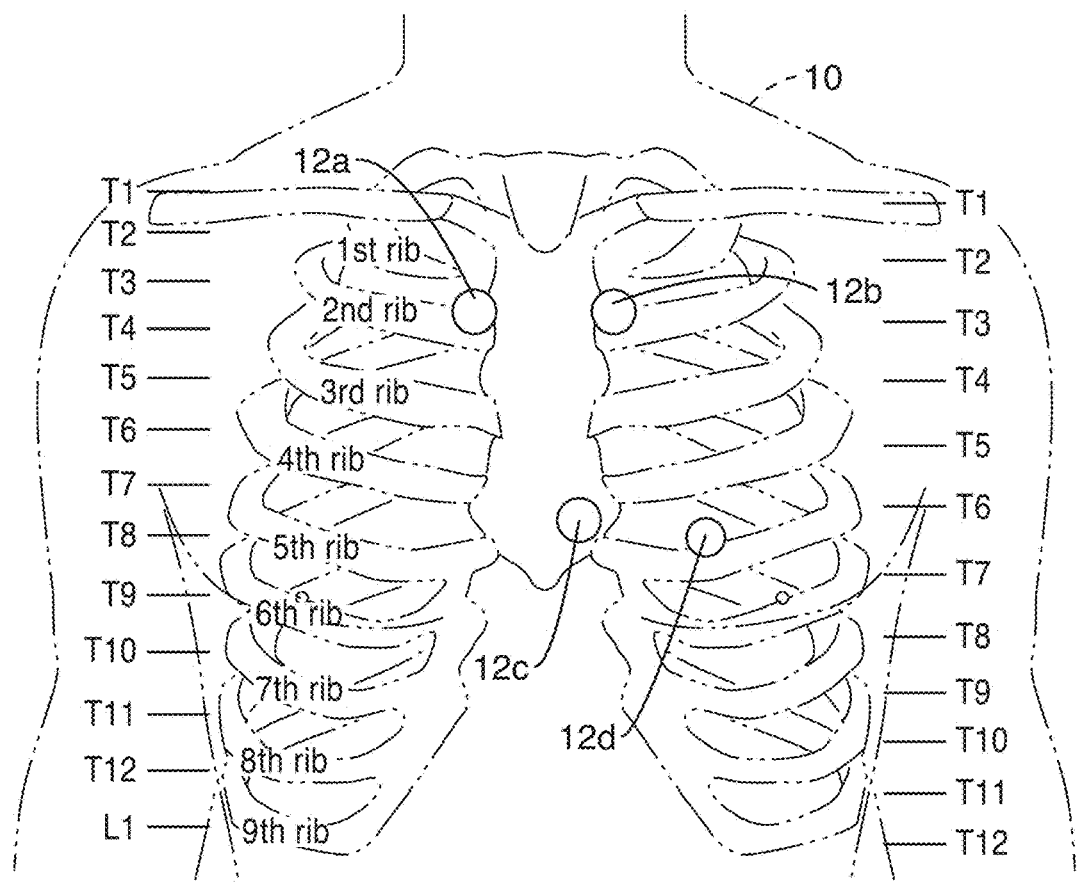
FIG. 2A shows an image of representative ICR acoustic sensor locations based on typical auscultatory sites used with standard stethoscope system.
Figure 3:
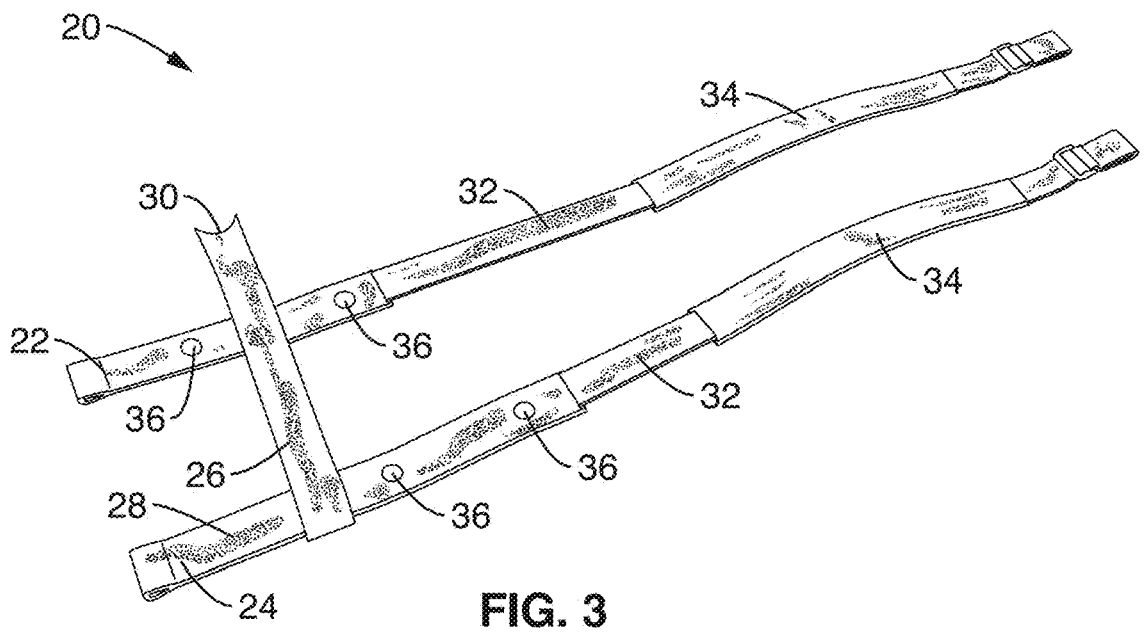
FIG. 3 illustrates a schematic diagram of an embodiment of the ICR sensor support without acoustic sensors.
Figure 4:
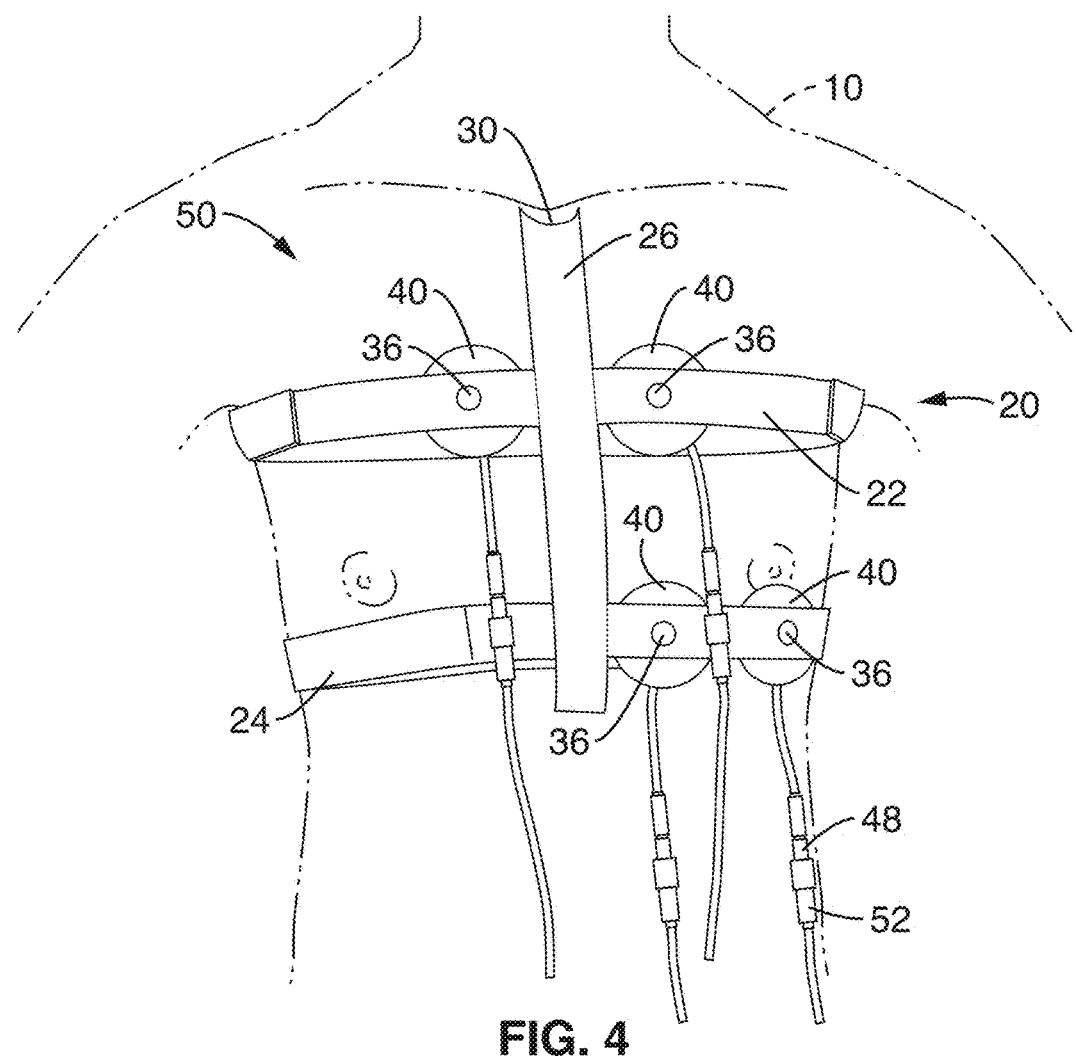
FIG. 4 illustrates a schematic diagram of the ICR sensor support with multiple acoustic sensors to form an ICR sensor application system positioned around the abdomen of the patient.

One ICR acoustic sensor 40 is shown in FIG. 1, however as shown in FIG. 3 and FIG. 4, multiple acoustic sensors 40 may be employed with ICR sensor support 20 to form an ICR sensor application system 50. As will be explained in further detail below, ICR sensor support 20 is configured to support ICR acoustic sensors 40 on the body of the patient 10 at locations based on typical auscultatory sites (FIG. 2A) used with standard stethoscope system, e.g. aortic site location 12a, pulmonary site location 12b, tricuspid site location 12c and mitral site location 12d.

Figure 2B:
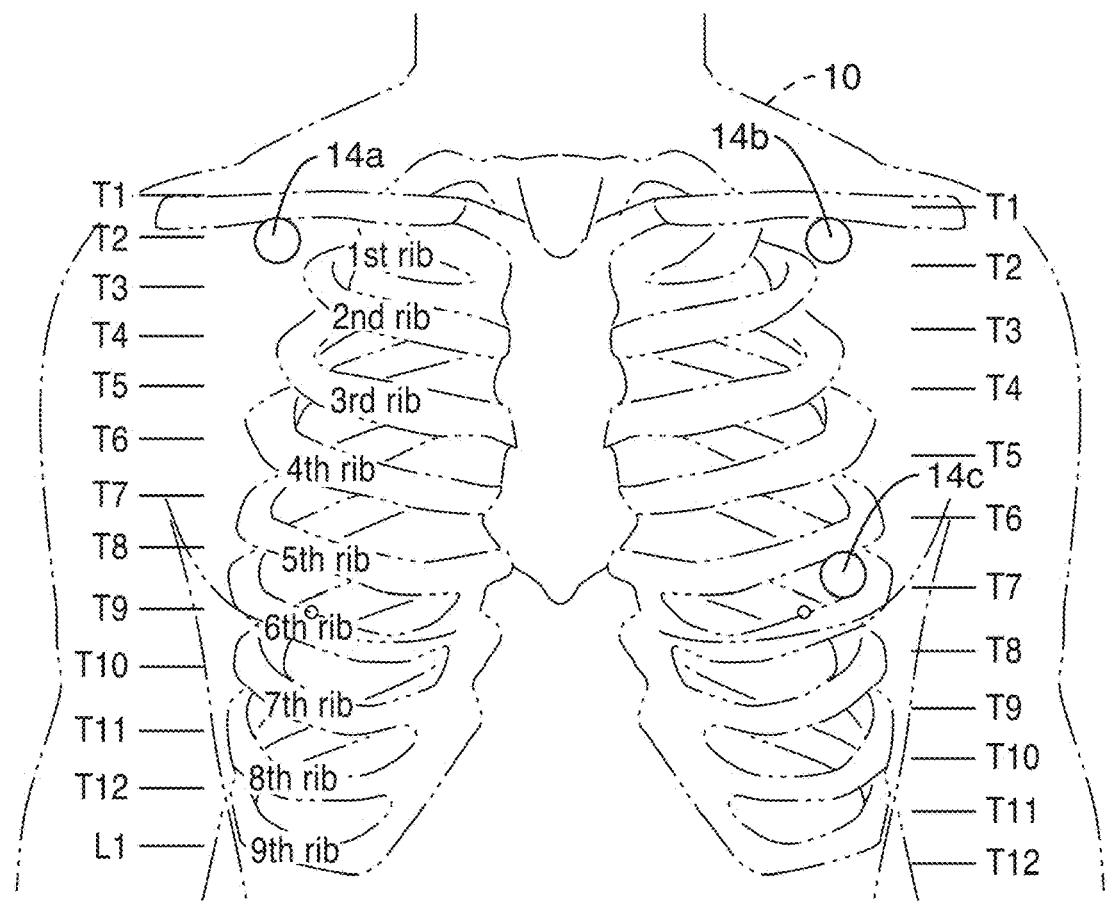
FIG. 2B shows an image of representative ECG sensor electrodes locations applied at conventional RA, LA, and LL monitoring sites.

In one embodiment, the ICR monitoring system 100 includes measurement capability for the ICR acoustic sensors 40 and standard three-lead, optically-isolated, ECG measurement. FIG. 2B shows an image of representative ECG sensor electrode 60 locations 14a, 14b, and 14c applied at conventional RA, LA, and LL monitoring sites, respectively.

In one embodiment, the ICR monitoring system 100 measures both acoustic signals from the four measurement sites 12a through 12d as well as the ECG signal from ECG sites 14a through 14c. Computation of EF is based on analysis of the S1 and S2 characteristics and the time of arrival of S1 and S2 events relative to the QRS event in the ECG signal as explained in further detail below.

In an alternative embodiment, the ICR monitoring system is configured to monitor only acoustic signals from the ICR acoustic sensors 40 using a PCG-gated segmentation method, as provided in further detail below. In such system, ECG sensors, or other sensor input, are not necessary.

2.1 ICR Sensor Application System

In a preferred embodiment shown in FIG. 3 and FIG. 4, the ICR sensor support 20 of FIG. 3 is placed around the upper abdomen of a patient 10 with ICR acoustic sensors 40 to form an ICR sensor application system 50. The ICR sensor application system 50 holds ICR acoustic sensors 40 in position (e.g. at auscultatory locations 12a-12d) to allow for continuous signal recording in a form that is comfortable for the patient, convenient and accurate for the care provider, and provides a low-cost disposable component enabling single-use.

FIG. 3 illustrates an embodiment of the ICR sensor support 20 without acoustic sensors 40. The ICR sensor support 20 includes two chest straps 22, 24 that are configured to be positioned horizontally around the patient. A vertical separator component 26 is fixed to the upper chest strap 22 and is configured to be releasably attached via a releasable fastener 28 (e.g. hook-and-loop) to the lower chest strap 24. The vertical separator component 26 coupling the two chest straps 22, 24 indicates the vertical position of the straps. A small semicircular indicator 30 at the upper end of the vertical separator 26 indicates the familiar and easily identified suprasternal notch of the sternum. The chest straps 22, 24 each include a pair of markers 36 that are configured to locate attachment of the ICR acoustic sensors 40 individually at preferred locations for acoustic monitoring within the abdomen/chest of the patient 10.

Each of the chest straps 22, 24 include flexible stiffener sections 34 and elastic sections 32 for application convenience. All materials, including the elastic sections 32, are preferably composed of latex-free, biocompatible materials.

In one embodiment, the ICR sensor support 20 is provided in a kit of varying sizes to match varying patient size, e.g. 5 sizes labeled X-Small, Small, Medium, Large, and X-Large. These sizes may be selected according to subject height according to Table 1.

FIG. 4 illustrates the ICR sensor support 20 with four acoustic sensors 40 to form an ICR sensor application system 50 positioned around the abdomen of the patient 10. With the semicircular indicator 30 at the upper end of the vertical separator 26 positioned at suprasternal notch of the sternum, the ICR acoustic sensors 40 are aligned at the proper locations for acoustic sensing, e.g. ICR acoustic sensors 40 on the upper chest strap 22 are aligned with the aortic site location 12a and pulmonary site location 12b, while the ICR acoustic sensors 40 on the lower chest strap 24 are aligned with tricuspid site location 12c and mitral site location 12d.

In one embodiment, the ICR sensor support 20 and/or ICR sensor application system 50 are configured as a disposable, single-use device ensuring proper and convenient attachment as well as patient comfort. In the embodiment shown in FIG. 4, identical acoustic sensors 40 are shown applied to a subject. Each of the acoustic sensors 40 may have male 48/female 52 lead connections that are color coded for attachment to the ICR patient monitor via leads 54.

Figure 5:
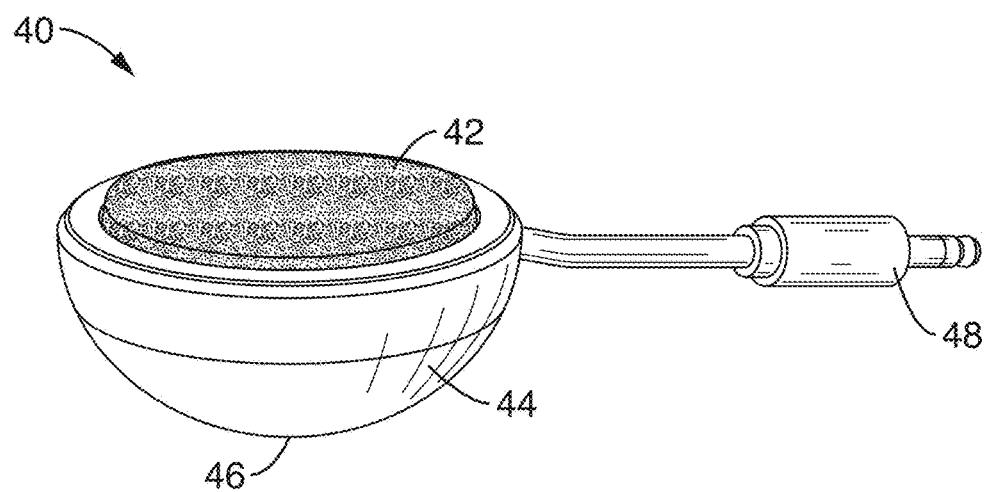
FIG. 5 shows a side view of an ICR acoustic sensor in accordance with the present description.

FIG. 5 shows a side perspective view of an exemplary ICR acoustic sensor 40 in accordance with the present description. ICR acoustic sensor 40 comprises a half-dome shaped housing 44 with a nitrile (latex-free) membrane 42. At the opposite end 46 of the housing from the membrane 42, a releasable attachment means (e.g. circular area of hook-and-loop material—not shown) may be positioned to enable attachment of the acoustic sensor 40 to the ICR sensor support 20 at the specified markers 36. It is appreciated that acoustic sensors 40, applied at each site, are connected to the patient monitor leads 54 with color-coded male connector 48 that matches the corresponding female connector 52.

In one embodiment, sensor attachment to the body of the patient 10 is straightforward with assurance for both vertical and lateral position with the following steps:

(a) The upper chest strap 22 of the ICR sensor support 20 is applied and positioned immediately below the underarm locations. The strap tension is adjusted for comfort to suit the girth of the patient.

(b) The lateral position is indicated by positioning the notch 30 of the vertical separator 26 aligned with the patient sternum.

(c) The chest strap 24 of the ICR sensor support 20 is positioned with its attachment at the lower end of the vertical separator 26. The strap tension is adjusted for comfort to suit the girth of the patient.

(d) Sensor positions are then indicated via markers 36 and the acoustic sensors 40 are applied. In one embodiment, acoustic sensors 40 are applied with a simple hook-and-loop attachment between the sensor 44 housing and the corresponding hook-and-loop section 28 at each chest strap 22, 24.

(e) ECG sensors may also be added at the LA, RA, and LL standard positions indicated in FIG. 2B.

(f) The color-coded interconnect cables/leads 54 are connected at male/female connectors 48/52 to couple each sensor to a corresponding input to the patient monitor 102.

(g) Sensor 40 attachment color assignment may also be assured by the presence of keyed connectors that allow only properly assigned sensor color codes to be applied.

3. ICR System Analytics

This section details methods used in data acquisition and signal processing for computing EF and other cardiac metrics in accordance with the ICR monitoring system 100 of the present description. The methods detailed below are preferably implemented as instructions in machine-readable code within one or modules of application programming 110, which may be executed on monitor 102 or other external processing device.

3.1 ECG Signal Processing and Analysis

Where an ECG-gated segmentation (described in further detail below) method is used, ECG signals measured using traditional ECG electrodes are used to enable timing and proper identification of phonocardiogram (PCG) acoustic signatures as belonging to S1, S2, or another part of the cardiac cycle. In each cardiac cycle, electrical depolarization of the ventricles causes a displacement in voltage observed in the ECG signal, known as the R wave. The R wave is usually the most prominent feature in the ECG signal. If the R wave can be accurately identified within each cardiac cycle, the signal can then be decomposed into individual cardiac cycles to segment the ECG signal. If the ECG and PCG are acquired synchronously, this same decomposition can be applied to the PCG. Thus, the primary objective of ECG signal processing when implemented in the methods of the present description is robust R wave detection.

R wave detection is complicated by several factors. First, the amplitude and morphology of the R wave can vary widely due to variations in ECG electrode placement or the presence of certain cardiac conditions. These causes also contribute to variability in the amplitude of the T wave. The T wave of the ECG reflects the electrical repolarization of the ventricles in the cardiac cycle. In some scenarios, this may result in R and T waves of similar amplitude. This creates difficulty when attempting to identify R waves based solely on amplitude criteria.

Further, several sources of noise can corrupt the ECG signal, including 1) power line interference, 2) electrode contact noise, 3) motion artifacts, 4) muscle contraction, and 5) baseline drift and amplitude modulation with respiration. Power line interference includes of 60 Hz noise that can be up to 50 percent of peak-to-peak ECG amplitude. Baseline drift and amplitude modulation often result from respiration by the subject, creating large periodic variations in the ECG baseline. Electrode contact noise is caused by degradation of coupling between the electrode and the skin. The level of noise induced is dependent upon the severity of the degradation. If there is complete loss of contact between the electrode and skin, the system is effectively disconnected, resulting in large artifacts in the ECG signal. If coupling is reduced but there is still some degree of contact between electrode and skin, a lower amplitude noise is introduced, which may persist if the coupling is suboptimal. Coupling issues can also be intensified by subject motion and muscle contraction, which can further affect the contact surface area between electrode and skin.

To mitigate these effects, one embodiment the ICR system 100 uses advanced preprocessing techniques, which may be implemented within application programming 110, comprising:

(a) Band-pass filtering the acquired ECG signal;
(b) Multiplication of the filtered signal by its derivative;
(c) Envelope computation;
(d) Identification of R waves in the computed envelope;
(e) Identification of corresponding peaks in the filtered signal; and
(f) Determination of R wave onset in the filtered signal.

Band pass-filtering is used to minimize the effects of baseline drift, powerline interference, and other noise sources while maintaining underlying ECG signals. A band pass filter can be defined by its lower and upper cut-off frequencies, and the region between these two frequencies is known as the pass band. While optimal cut-off frequencies may vary based on hardware, an example embodiment may have a passband between 1 Hz and 30 Hz. There exist many well-defined filter design tools both for Infinite Impulse Response (IIR) and Finite Impulse Response (FIR) filters which allow for the design of bandpass filters based on desired specifications for block-band rejection, passband attenuation, filter order, and other performance specifications. In the ICR system, application of a bandpass filter can significantly improve signal to noise ratio, and subsequent preprocessing is performed on the filtered signal, f(t).

In typical ECG signals, the R wave is characterized by a large amplitude, and selection of R wave candidates based purely on amplitude can be effective. However, in some cases, T waves can become as prominent as R waves, and this straightforward approach is rendered ineffective. To mitigate the effect of elevated T waves, the ICR system exploits another characteristic of the R wave, namely it's higher frequency content relative to typical T waves. By computing the derivative of the signal f(t), an operation that amplifies high frequency content, a signal with exaggerated R wave amplitude is generated. Subsequent multiplication of f(t) with its derivative yields a new signal, g(t), that greatly emphasizes R waves relative to the sometimes-problematic T wave.

The envelope of the resulting signal, g(t), is computed using the Hilbert transform, and this envelope is subsequently low-pass filtered with a cutoff frequency of 8 Hz to further amplify the R wave, and the resulting envelope is normalized by dividing by its 98th percentile value. Note that this approach is used rather than division by the maximum value to reduce the effects of spurious outliers in the envelope.

Peak detection of the resulting signal leverages known peak-detection algorithms with minimal peak height set to 50% of the maximum envelope height. Several conditions can be imposed to eliminate peaks not likely to be associated with R waves. For example, excessive amplitude or an excessive number of peaks in rapid succession can be used to guide removal of false peaks prior to subsequent processing.

Once the R wave peak locations have been identified in the envelope, R wave onset is determined as the last value above a certain threshold. An example threshold here might be 50% of the envelope peak.

Figure 6A:
FIG. 6A through FIG. 6E show images of an R wave detection process on clean ECG signal.
Figure 6B:
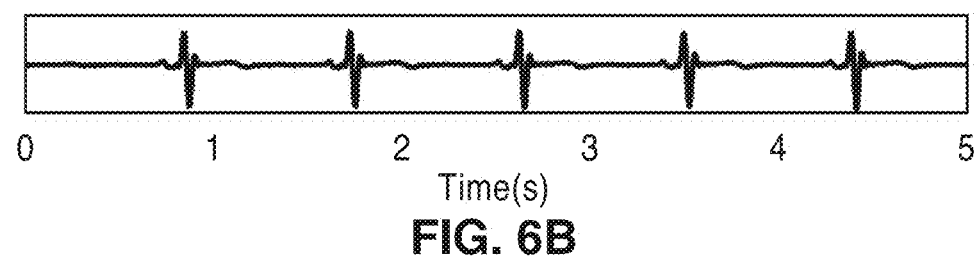
Figure 6C:
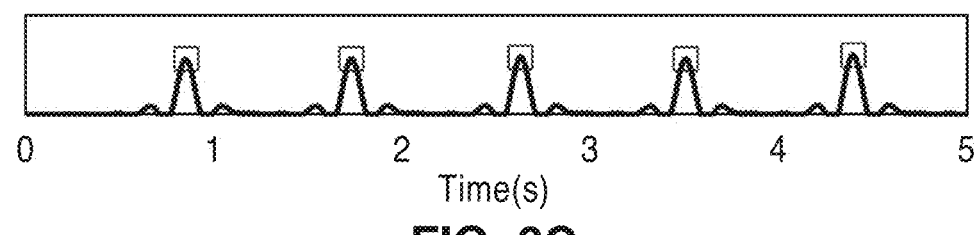
Figure 6D:
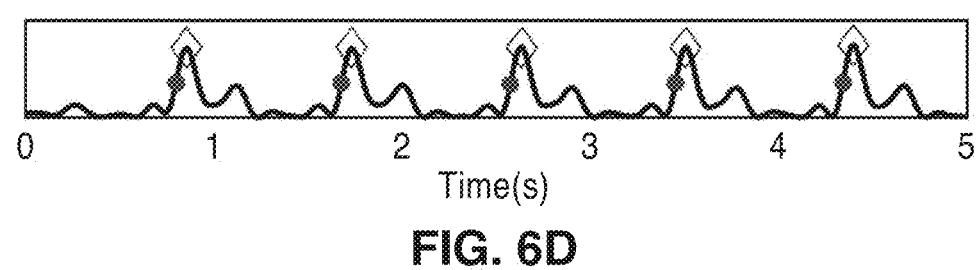
Figure 6E:
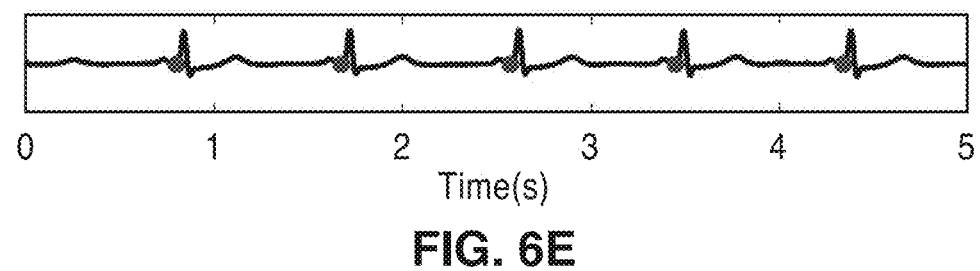

FIG. 6A through FIG. 6E show an exemplary R wave detection process on clean ECG signal. FIG. 6A shows the raw ECG signal. FIG. 6B shows the derivative of filtered ECG signal. FIG. 6C shows the envelope of function resulting from multiplying signal by its derivative, with detected peaks marked by squares. FIG. 6D shows the envelope of filtered signal, with detected peaks marked by diamonds, and R wave onset marked by solid circles. FIG. 6E shows the filtered ECG signal, with R wave onset marked by solid circles.

3.2 PCG Signal Processing
3.2.1 Noise Suppression

The PCG signal is also susceptible to noise from a wide variety of sources such as involuntary subject activity, voluntary subject activity, external contact with sensor, and environmental noise.

Involuntary subject activity includes involuntary physiological activity of the subject, such as respiratory and digestive sounds. Another common noise source in this group is the microscopic movement of tissue beneath the sensor, even with a seemingly motionless subject. This motion causes persistent fluctuations in the PCG signal that are usually of relatively low amplitude. If the cardiac signal strength is low, however, this noise can mask underlying cardiac events.

Voluntary subject activity includes activity such as speech and subject motion. These noise sources will generally create large disturbances in the PCG signal. Similarly, external contact with the sensor housing by another object such as clothing or a hand can also produce large artifacts in the signal.

Environmental noise generally includes all external sources of noise not involving the subject or the sensor. This may include non-subject speech, background music/television, and hospital equipment noise. With proper coupling of the sensor to the tissue, such noise factors typically have minimal effect on PCG signal quality, except for in extreme cases.

PCG signal preprocessing comprises band-pass filtering followed by Short-Time Spectral Amplitude Log Minimum Mean Square Error (STSA-log-MMSE) noise suppression. Band-pass filtering may be performed with cut-off frequencies of 25 and 100 Hz, which has been found to preserve PCG signals while reducing the amplitude of out-of-band noise sources.

In the method of the present description, a model of signal noise is generated, and short time segments of data are considered. A probability of the presence of acoustic activity other than noise is computed for each time segment, and a gain is computed as a function of this probability. Gain is low for low probabilities and approaches unity for high probabilities, thereby reducing the amplitude of purely noise-segments of audio. It should be noted that these models and corresponding gains are considered in the frequency domain. Conversions to frequency domain are performed using the Fast Fourier Transform (FFT), and conversions back to the temporal domain are performed using the Inverse Fast Fourier Transform (IFFT).

For PCG analysis, adaptations to the STSA-log-MMSE algorithm can be made. Whereas typical STSA-log-MMSE applications generally require a recording of known noise-only data, pre-existing knowledge of the timing of the cardiac cycle based on ECG segmentation can be leveraged to determine regions of acoustic inactivity. For example, it is known that within each cardiac cycle there will be regions that contain no cardiac sounds. Even if all cardiac sounds, including murmurs, are present, there are regions without such sounds. Thus, the regions of each cardiac cycle with RMS energy in the $25^{th}$ percentile are likely to be characterized by minimal cardiac acoustic signature. This allows for online generation of noise models and for adaptive updating of such models.

Figure 7A:
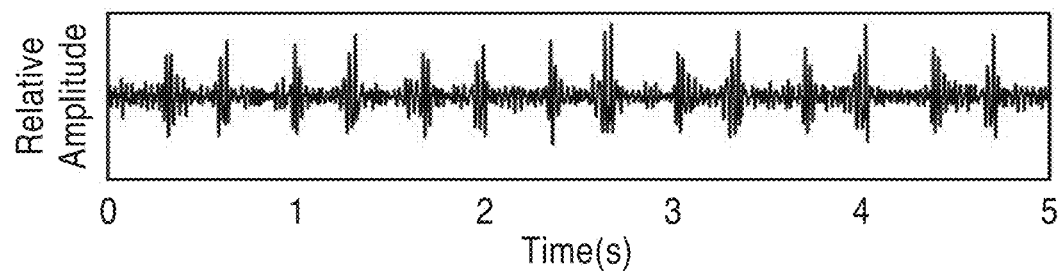
FIG. 7A through FIG. 7D illustrate an exemplary PCG signal noise suppression scheme in accordance with the present description.
Figure 7B:
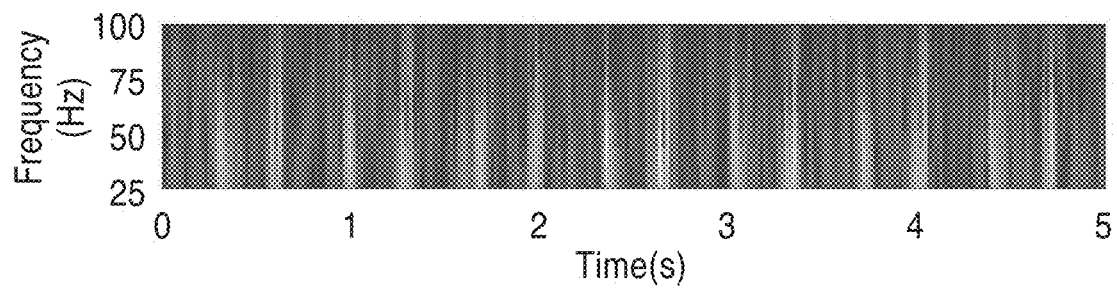
Figure 7C:
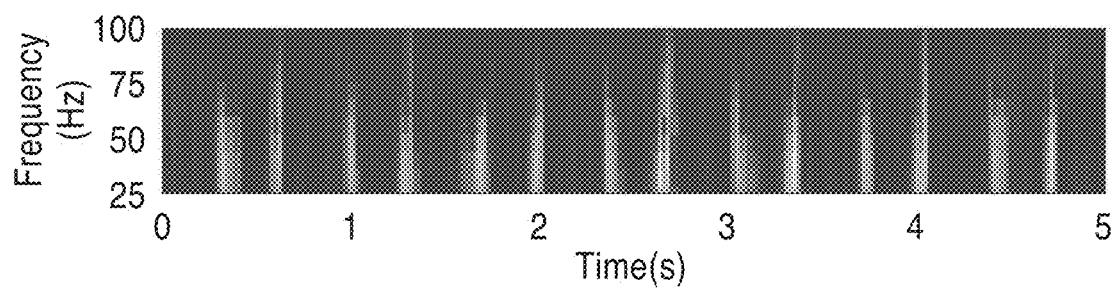
Figure 7D:
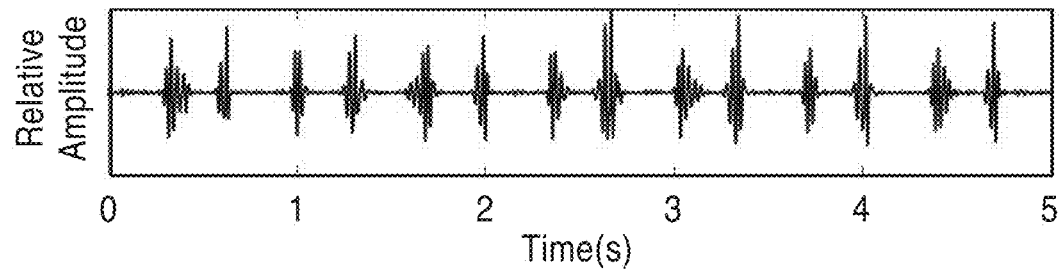

FIG. 7A through FIG. 7D illustrate an example of PCG signal noise suppression in accordance with the present description. FIG. 7A shows the original band-pass filtered signal. FIG. 7B shows a spectrogram of original signal. FIG. 7C shows a spectrogram of the de-noised or noise-suppressed signal, which demonstrates a significant reduction in noise. FIG. 7D shows the final de-noised signal, also demonstrating a significant reduction in noise.

3.3 Signal Segmentation

PCG signal analysis typically comprises three main stages: segmentation, feature extraction, and classification/regression. In the segmentation stage, cardiac acoustic events are detected and labeled. These events may include the S1, S2, S3, and S4 sounds, as well as murmurs. In a preferred embodiment, the ICR system 100 leverages primarily the fundamental heart sounds, S1 and S2, as these events possess the critical information needed for our objective of estimating ejection fraction (EF) via analysis of PCG signals.

The present description details two exemplary methods of PCG signal segmentation, hereinafter described as PCG-gated segmentation and ECG-gated segmentation. In PCG-gated segmentation, the PCG signal is segmented by sole examination of the PCG signal itself, without any complementary information from a synchronous ECG signal. Generally, in this approach, there is first a detection stage, in which an event detection method is applied to locate heart sounds. Here, signal processing methods are applied to emphasize regions of cardiac activity in the signal. Then, a decision method is applied to identify heart sounds based on certain predefined criteria.

Next, in the labeling stage, the sounds are labeled as one of the types described above. Quite often, this stage focuses mainly on the S1 and S2 sounds. Here, the interval duration between successive events, as well as characteristics of the events themselves, may be used to identify which group a certain event belongs to. The interval between S1 and S2 of the same cardiac cycle is the systolic interval, and the interval between S2 of one cardiac cycle and S1 of the next cardiac cycle is the diastolic interval. However, in direct PCG segmentation, it is unknown a priori where the breakpoints of each cardiac cycle lie. Thus, when presented with two consecutive events, it can be challenging to determine whether they correspond to the S1 and S2 events of the nth cardiac cycle, or the S2 event of the nth cycle, and the S1 event of the n+1th cycle.

Finally, in the decomposition stage, the PCG signal is decomposed into individual cardiac cycles, with the corresponding events and intervals between events occurring during each cycle attributed to it. This allows for analysis of each cardiac cycle individually.

In one embodiment of the ICR system 100, an ECG-gated framework is implemented that analyzes the ECG signal, and in particular the R wave onset, to enable timing of PCG signal segmentation. This method utilizes short-time periodicity of the ECG and PCG signals, a property that exists even in cases of abnormal heart rate.

To ensure periodicity, the PCG signal is analyzed in segments containing two consecutive cardiac cycles. Assuming the systolic intervals of consecutive cardiac cycles are consistent (which we have found to be the case, even in conditions of arrhythmia), performing correlation method analysis on such a segment allows for accurate detection and labeling of S1 and S2 sounds.

The first step in PCG segmentation is the generation of PCG envelopes from the processed, noise-reduced signal described above. Envelopes may be generated using the Hilbert transform or by computing the absolute value of the signal and passing it through a low-pass filter. Several different corner frequencies may be considered, and several envelopes may be generated and used for subsequent processing.

The envelope may be further processed by applying a threshold value to remove low-level noise. Finally, the signal may be adjusted by raising it to some power less than 1, a transform which tends to normalize the heights of peaks in the envelope such that all peaks are weighted approximately the same.

The envelopes are subsequently analyzed in segments containing two heartbeats, a preliminary segmentation that is enabled by analysis of the high-quality ECG signals generated previously. Each heartbeat is processed as the second event in one window and as the first event in the next window. As such, each cardiac cycle is analyzed twice, thereby increasing the likelihood of proper detection of that beat.

Figure 8A:
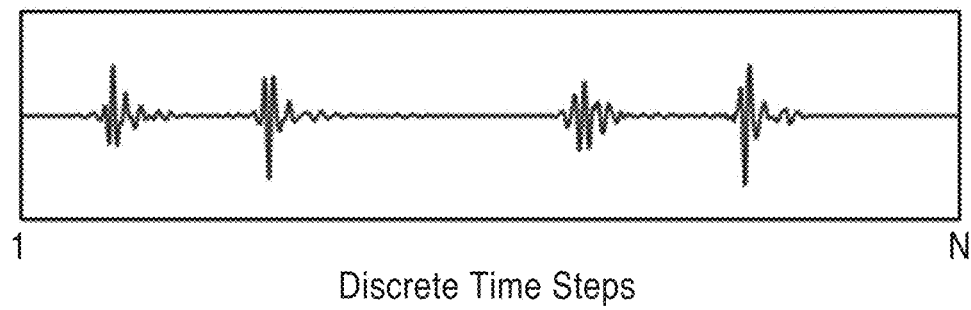
FIG. 8A through FIG. 8C show plots of the PCG signal segment, low-frequency envelope and autocorrelation of consecutive cardiac cycles, respectively.
Figure 8B:
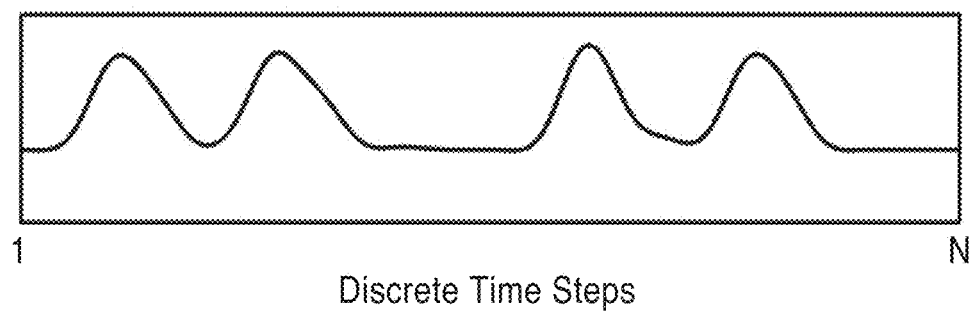
Figure 8C:
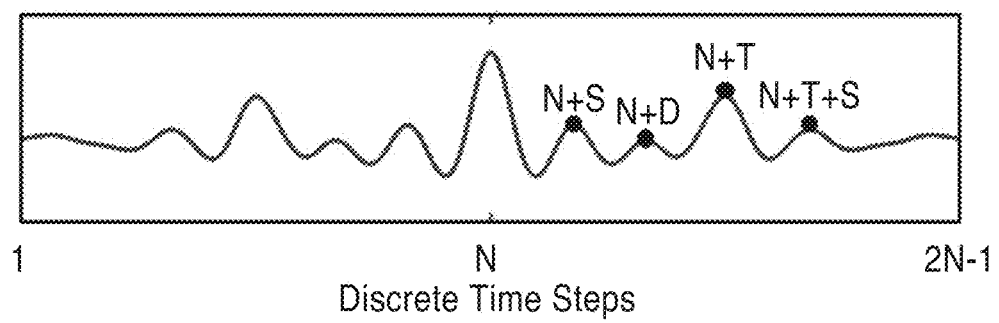

The autocorrelation function is applied to each two-beat envelope. This operator is commonly used to detect periodicity in signals, and this property is useful in PCG analysis. This process is highlighted in FIG. 8A through FIG. 8C. FIG. 8A shows a plot of the PCG signal segment of consecutive cardiac cycles. FIG. 8B shows a plot of the low-frequency envelope of corresponding segment. FIG. 8C shows a plot of the autocorrelation of low-frequency envelope. In FIG. 8C, several of the peaks are labeled by the corresponding intervals represented. It should be noted that there is a difference in scaling in the x axis between FIG. 8A through FIG. 8C.

The envelope shown in FIG. 8B is subjected to the autocorrelation operator, resulting in the symmetric signal, a(t), shown in FIG. 8C. a(t) shows a central peak, corresponding to the dot product of the envelope with itself with zero-time shift. There is also a second primary peak that is shifted by one period, T, relative to this central peak. This corresponds to the dot product of the envelope with an envelope shifted by T, such that the peaks associated with one heartbeat are aligned with those of the subsequent beat, thereby resulting in positive interference. Also evident in FIG. 8C are smaller peaks shifted by the systolic and diastolic periods, which are caused by overlap of S1 peaks with S2 peaks.

The autocorrelation described above enables computation of a valuable quality metric. For high quality PCG recordings, the peak at N+T is sharp and prominent. This prominence is quantified as the difference in its height relative to the lowest points surrounding it. This signal quality index is used to quantify signal quality, which is of critical importance in guiding subsequent algorithms. For example, if one sensor is characterized by low quality relative to others, its role in a classifier may be devalued or de-weighted relative to that of others. Alternatively, this feature can be used to alert system operators of insufficient signal quality, indicative of poor sensor placement.

Figure 9A:
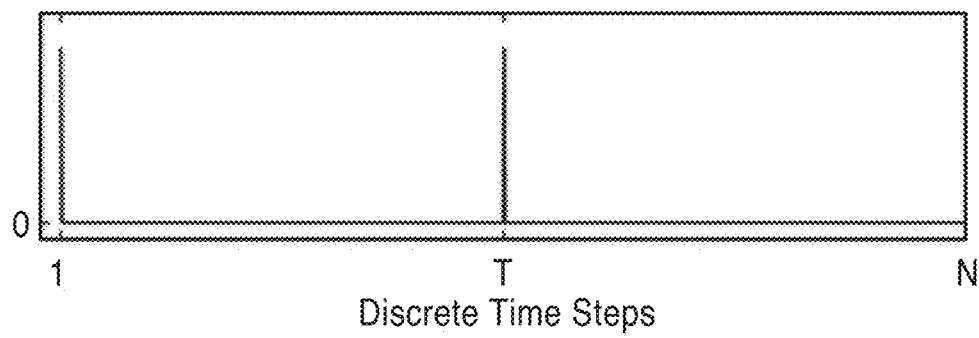
FIG. 9A through FIG. 9C show a cross-correlation method of estimating S1 locations.
Figure 9B:
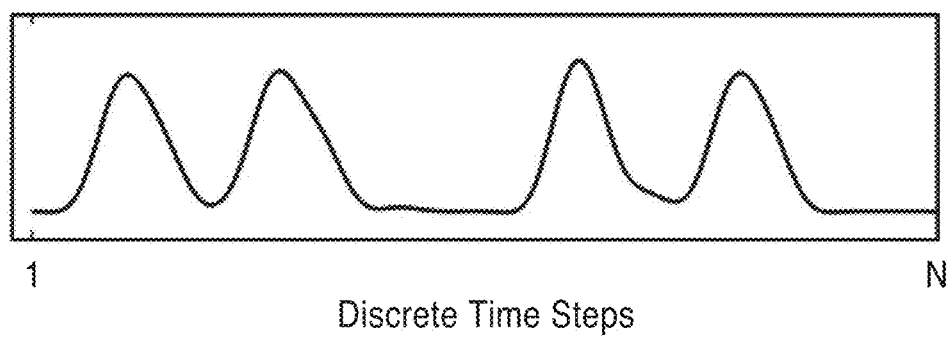
Figure 9C:
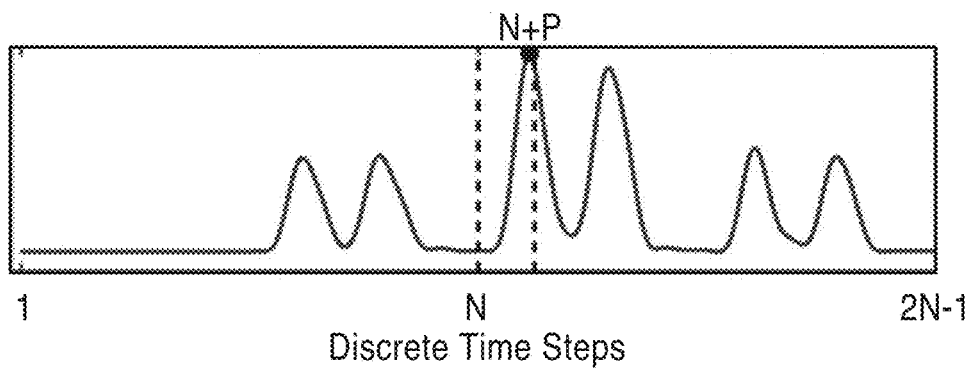

With the cardiac period, T, now determined, the next step is to determine the location of individual cardiac events within the cardiac cycle. To locate S1 events, a comb function is generated whose value is zero at all locations except at integer multiples of the period. Convolution of this function with the PCG envelope yields a series of peaks as the delta functions in the comb pass through peaks in the envelope. When these deltas align with S1 events, a large peak is generated, and the offset of this peak is equal to the offset of the S1 events in the PCG signal. This yields a search interval in the original PCG signal within which the S1 event is known to occur. This process is demonstrated in FIG. 9A through FIG. 9C, which show a cross-correlation method of estimating S1 locations. FIG. 9A shows a plot of function f(n). FIG. 9B shows a plot of the low-frequency envelope of the PCG signal segment. FIG. 9C shows a plot of the cross-correlation of f(n) with low-frequency envelope. In FIG. 9C, the S1 peak search interval marked with dashed lines.

Figure 10A:
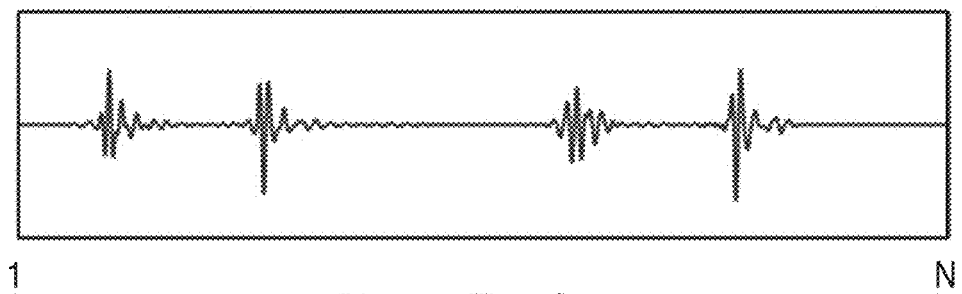
FIG. 10A through FIG. 10C show a method for autocorrelation of the high-frequency envelope segment for systolic interval estimation.
Figure 10B:
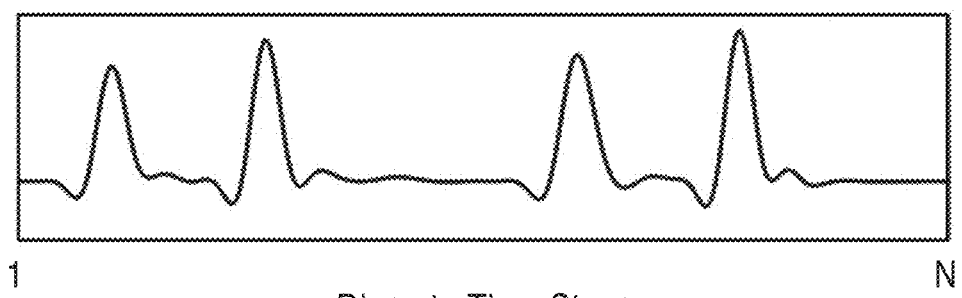
Figure 10C:
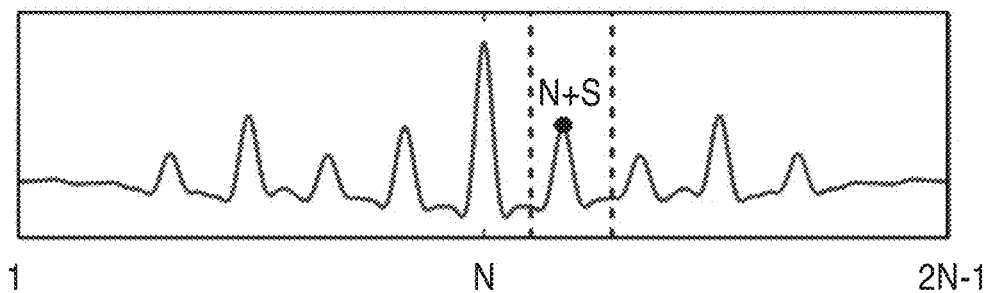

With S1 now located, the remaining task is to determine S2 location. To this end, the autocorrelation, a(t), of the PCG envelope is revisited. As described above, a(t) contains secondary peaks associated with the systolic and diastolic tie intervals. The systolic interval is given by the location of the first peak after the central peak as shown in FIG. 10A through FIG. 10C. Thus, the search region for S2 events is confined to the area around this peak. Because S2 events are not always evident in PCG signals, these peaks may not be discernible, and a search for a peak in this vicinity may yield peaks in regions where the S2 event is known not to occur. Thus, the search is limited to the region bounded by N+0.2 T and N+0.55 T. Peaks outside this interval are not considered. This process is demonstrated in FIG. 10A through FIG. 10C, which illustrate autocorrelation of the high-frequency envelope segment for systolic interval estimation. FIG. 10A shows a plot of the PCG signal segment. FIG. 10B shows a plot of the high-frequency envelope. FIG. 10C shows the resulting autocorrelation of the high-frequency envelope. In FIG. 10C, the dashed lines represent boundaries of N+0.2 T<n<N+0.55 T.

As a final step in PCG signal segmentation, false event removal methods may be applied. This may leverage timing and duration properties, as well as other known signal characteristics. For example, the time interval between onset of the R wave and onset of the S1 sounds is typically very consistent, a property than can be leveraged to remove detected S1 peaks that occur significantly before or after the expected time.

Additionally, cardiac events are characterized by durations of 20 ms to 250 ms. If a detected peak has a duration outside of this range, it is likely an artifact of noise and can be removed from consideration.

3.4 PCG Features and Feature Extraction 3.4.1 Time and Amplitude Features

Extensive studies performed on healthy and afflicted individuals have enabled exploration and discovery of features shown to correlate with Ejection Fraction (EF). These features may leverage Temporal and Amplitude characteristics (TA), Frequency characteristics, or other signal characteristics.

Figure 11A:
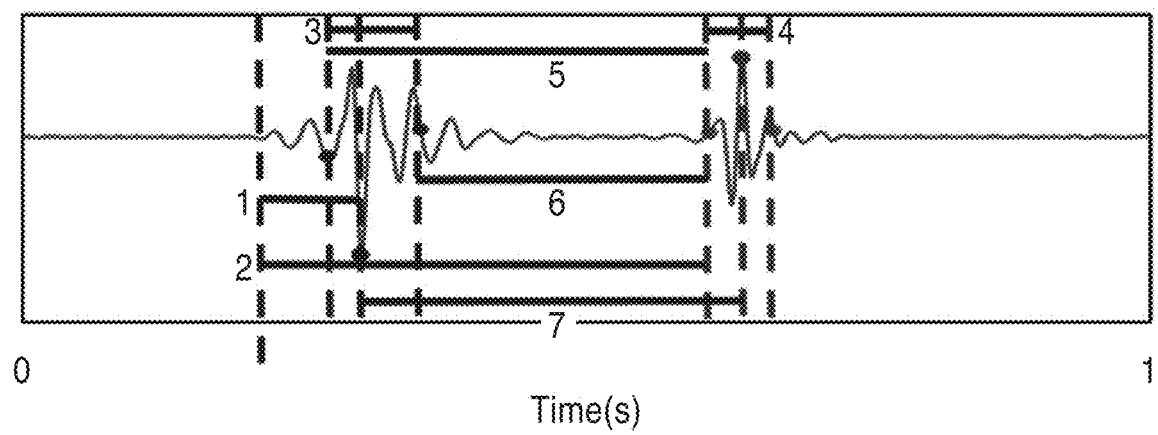
FIG. 11A and FIG. 11B show temporal feature extraction of the PCG signal cardiac cycle.
Figure 11B:
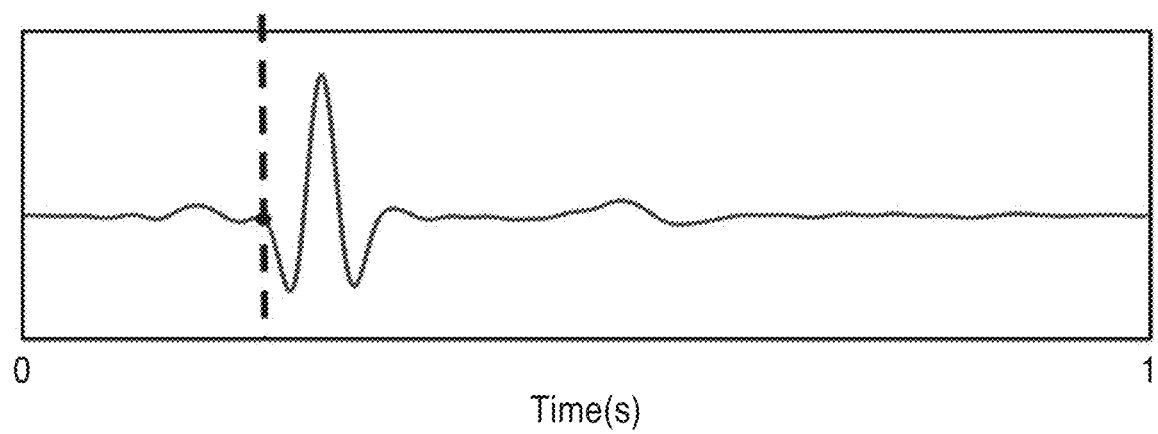

FIG. 11A and FIG. 11B show temporal feature extraction of the PCG signal cardiac cycle. FIG. 11A shows the PCG signal and extracted features 1-7. FIG. 11B shows the corresponding ECG signal.

Referring to FIG. 11A, a large number of TA features have been extracted and determined to be of value in computing EF. The extracted temporal features include, but are not limited to: 1) electromechanical activation time (EMAT), defined as the interval between the QRS complex onset and the S1 peak 2) $QS_2$, the total electromechanical systolic interval, measured from the onset of the QRS complex to the first high-frequency vibration of the aortic component of the second heart sound, 3) S1 duration, 4) S2 duration, 5) mitral cessation-to-opening time (MCOT), 6) left ventricular ejection time (LVET), measured from the beginning upstroke to the trough of the incisura of the carotid arterial pulse tracing, and 7) left-ventricular systolic time (LVST), defined as the interval between the S1 peak and the S2 peak. S1 and S2 duration are computed as the intervals between the endpoints of the respective events. As we do not have access to the carotid arterial pulse signal, LVET is here estimated as the interval between the end of the S1 event and the start of the S2 event. Mitral cessation-to-opening time is the interval from the cessation to onset of mitral inflow. It can be estimated from the PCG signal as the interval between the start of the S1 event and the start of the S2 event.

Other features may be derived from the envelope of the signal. For example, the time difference between the S2 and S1 envelope peaks has been studied extensively.

Temporal features may also be normalized by the cardiac cycle period, yielding additional normalized temporal features. Further, PCG data allows computation of the Tie index, also known as the Myocardial Performance Index, as the ratio (MCOT-LVET)/LVET.

In addition to temporal characteristics, the feature set may also include amplitude characteristics of the S1 and S2 events as well the diastolic and systolic intervals. These features can be derived from both the PCG signal and its envelope. For both S1 and S2 event intervals, the following features have been considered: root-mean-square (RMS) of PCG signal segment normalized by RMS of PCG signal of entire cardiac cycle; peak amplitude of PCG signal segment, normalized by variance of PCG signal of entire cardiac cycle; and peak amplitude of envelope segment, normalized by the envelope mean value for the entire cardiac cycle. For the diastolic and systolic intervals, examined features include RMS of the PCG signal segment normalized by RMS of PCG signal of entire cardiac cycle. This normalization is performed to reduce feature dependency on absolute amplitude. Amplitude features can also be combined in a number of ways, including ratiometric analysis of S1 and S2 features (e.g. S1 RMS:S2 RMS), as well as the ratios of the S1 and S2 RMS to the diastolic and systolic RMS.

Figure 12A:
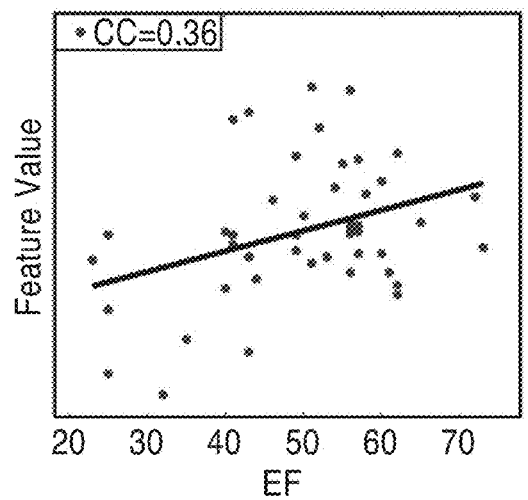
FIG. 12A through FIG. 12C show PCG feature extraction and correlation with EF.
Figure 12B:
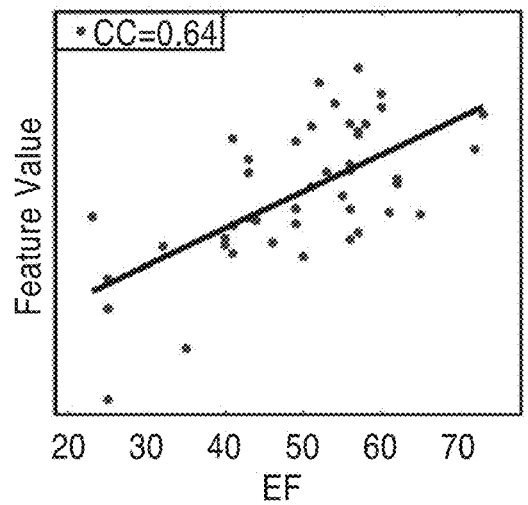
Figure 12C:
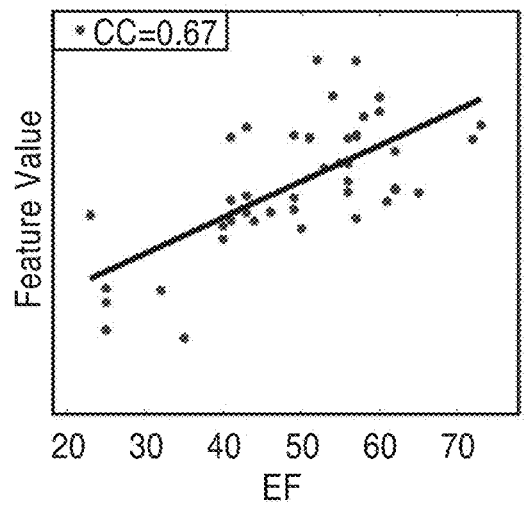

Finally, linear and nonlinear combinations performed on temporal and amplitude features yield temporal-amplitude features. One such example would be the multiplication of the S1 RMS by the time difference of S1 and S2 peaks in the signal envelope. FIG. 12A through FIG. 12C show PCG feature extraction and correlation with EF. FIG. 12A shows EF vs. time interval between S1 and S2 envelope peaks FIG. 12B shows EF vs. S1 RMS. FIG. 12C shows EF vs. multiplication of features in FIG. 12A and FIG. 12B. CC=Pearson's correlation coefficient. As is shown in FIG. 12A through FIG. 12C, this combination of features demonstrates stronger correlation with EF than the individual temporal and amplitude components.

3.4.2 Frequency Characteristics

Figure 13A:
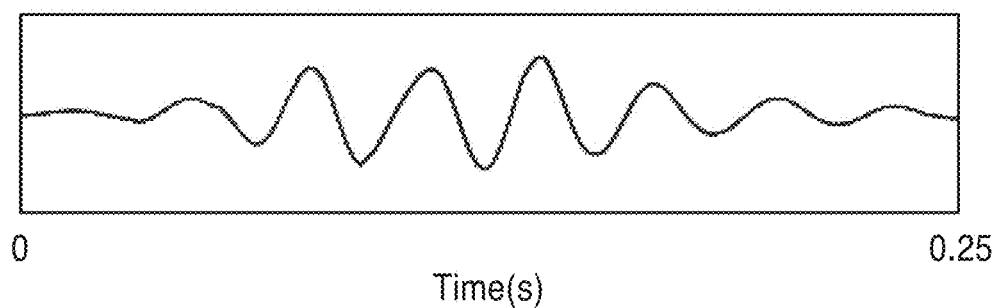
FIG. 13A through FIG. 13C show AM-FM decomposition of an S1 event.
Figure 13B:
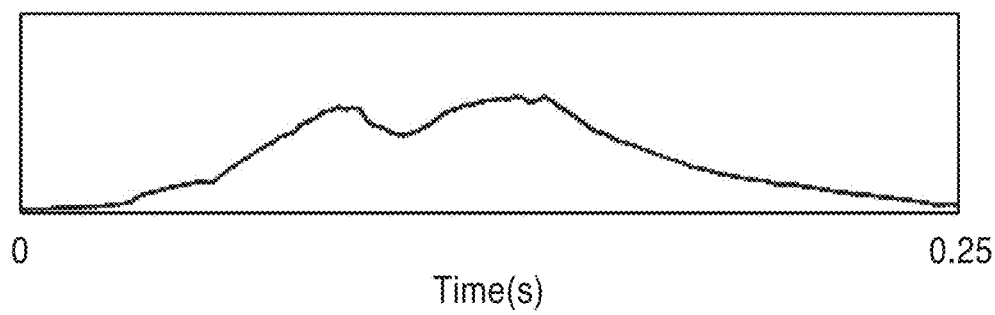
Figure 13C:
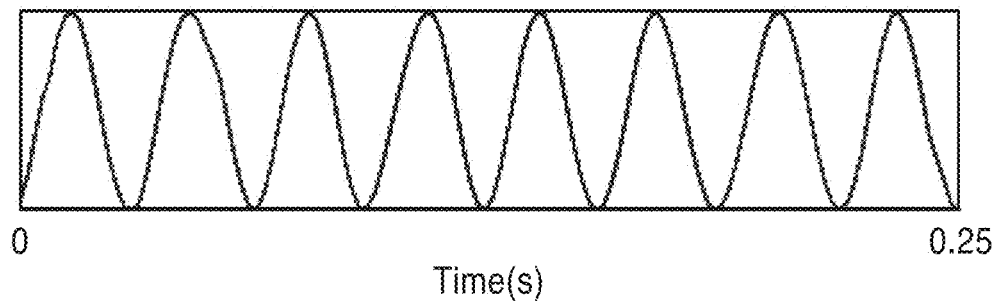

The frequency domain has been found to yield further sets of valuable features. In particular, an AM-FM decomposition of S1 and S2 sounds was found to provide a powerful dimension-reduction capability and to enable discovery of new features correlating strongly with EF. FIG. 13A through FIG. 13C show AM-FM decomposition of an S1 event. FIG. 13A illustrates the PCG signal segment of an S1 event. FIG. 13B shows the AM component. FIG. 13C shows the FM component (carrier signal).

In an AM-FM decomposition, a PCG signal is represented as an envelope b(t) multiplied by a carrier signal, f(t), which is defined as having unit amplitude. By dividing the original signal by a model of b(t), a carrier signal with unit amplitude is recovered, and the FFT of this signal yields its frequency content. This process, defined as Phonocardiogram Carrier Signal Analysis (PCSA), has been found to yield features strongly correlated with EF.

For example, one valuable feature has been defined as the ratio between the energy content contained in a high-frequency band of f(t) relative to that contained in a low-frequency band. The energy associated with a band is computed as the sum of the FFT of f(t) with limits provided by the upper and lower limits of the band. For example, a band might be defined by lower and upper limits of 10 Hz and 15 Hz respectively, and the energy contained in this band would be computed as the sum of the FFT from 10 Hz to 15 Hz. By defining a low and a high frequency band, computing the associated energy for each band, and then computing the ratio, $R_{PCSA}$, of these energies, a powerful PCSA feature can be computed.

3.5 Optimization of PCSA Frequency Ratios

The computed quantity, $R_{PCSA}$, is parameterized by four values, namely the lower and upper limits of the lower and upper frequency bands. In order to optimize this computed value for subsequent EF computation, these four values must be selected based on training data. To this end, the Pearson Correlation Coefficient (PCC) as well as the linear regression correlation coefficient are considered. These two values quantify the extent to which an input variable (in this case, $R_{PCSA}$) correlates with an output variable (in this case, EF). A zero value indicates zero correlation, and an absolute value of one indicates perfect correlation. Thus, selection of optimal parameters in computing $R_{PCSA}$ is equivalent to maximizing the correlation coefficient between $R_{PCSA}$ and EF with these four frequency values as inputs. Constraints may be placed on the frequency bands to reduce the size of the four-dimensional search space. For example, the upper limit of a frequency band must be larger than its lower limit. Further, the lower limit of the high frequency band must be above the upper limit of the low frequency band.

A number of methods have been used to perform this optimization. A brute force method can be used that considers all possible combinations of frequency bands, computes the result correlation coefficient for each combination, and records the maximum such coefficient. Alternatively, a constrained non-convex optimization routine may be executed a large number of times with randomly selected initial seeds, each time converging to a local maximum. The largest such local optimum would be considered the best solution. Finally, a lower dimensional search space may be considered by, for example, constraining the width of the upper and lower bands and only varying their respective center frequencies. The resulting two-dimensional optimization can be performed much faster at the cost of potentially overlooking optimal solutions. Any of the above methods can be computed more rapidly via a highly parallelized computing structure such as a cluster or network of computing machines.

3.6 Tiered Classification Methodology

The features described above are used by a multi-tiered series of Neural Network (NN) classifiers to compute an associated EF value. In this configuration, a global classifier is first used to assign subjects to one of several subgroups. This classifier computes an EF estimate, and subjects are assigned to subgroups based on defined thresholds. The subgroups may, for example, be defined as UltraLow EF, Low EF, medium EF, and high EF, although other subgroup divisions are possible.

Once a subject is assigned to a subgroup, a new set of features specific to the assigned subgroup is computed. These features are then used as inputs for an NN classifier designed specifically for that EF subrange.

As an example, the global classifier may assign to a subject an EF value of 38, which would place the subject in the low EF category. Thereafter, a new set of features would be computed for this subject, and the Low EF NN classifier would be used to assign an EF value, which would subsequently be reported as the computed EF value. As an alternative example, the global classifier may assign to a subject a value of 68, which would place the subject in the High EF subgroup. Thereafter, a new set of features is computed, and the subject is re-classified using the High EF classifier. The resulting value would be outputted as the computed EF value associated with that subject.

3.7 Detection of EF Outlier Conditions

There are a number of medical conditions that may cause ICR computed EF to deviate significantly from values measured via echocardiography. For example, in the case of hypertrophic cardiomyopathy, heart walls become enlarged, resulting in reduced end-diastolic volume. In these cases, even a reduced ejection volume may result in a very high EF, placing the subject in a regime known as hyperdynamic EF.

The physiology presented in this and other cardiac conditions may present difficulties in application of the classifiers described above. As such, it is critical to enable discriminators that detect such conditions and enable separate EF computation.

PCSA analysis has proven useful to this end as well. Hyperdynamic subjects encountered in clinical trials have exhibited unique PCSA characteristics enabling pre-classification as hyperdynamic. Specialized PCSA ratios have been developed to effectively separate or discriminate such subjects.

3.8 System State Machine

Proper EF classification in clinical use utilizes proper sensor placement, acquisition of sufficient high-quality data, classification into EF subgroups, and subsequent computation of EF.

To initiate a measurement, a clinician places sensors in the prescribed locations and then begins a recording. The initial phase of the recording enables the clinician to fine-tune sensor placement until sufficient data quality has been detected. The system remains in this sensor adjustment state until high-quality data has been received from a sufficient number of sensors for a sufficient period of time.

After successful completion of this phase, the system enters the calibration phase, in which data is recorded for a preset amount of time. If data quality deteriorates excessively during this phase, the system transitions back to the sensor adjustment state.

During the calibration phase, there is not yet sufficient data to pre-classify the subject into an EF subgroup. As such, it is not possible to report EF during this phase. However, in order to reduce delay associated with EF computation, features and EF values associated with all subgroup classifiers are computed during this time. Once the calibration phase has elapsed, the global EF classifier is able to compute an EF value and subsequently pre-classify the subject into one of the subgroups. The pre-computed EF values for the corresponding classifier are retrieved, and their average is reported.

3.9 Surgically Implanted Sensor System

In addition to previously described system embodiments, a system configuration involving implantable sensors may be implemented. Whereas previous systems considered the used of sensors mounted external to the body, the small size and low-power requirements of acoustic and pressure transducers enables such devices to be surgically implanted in desired locations. The increased proximity to sound source yields improved coupling and improved signal quality. Further, the effect of external disturbances is reduced.

Such an embodiment may operate continuously or episodically, and raw or processed data may be transmitted to a device external to the subject. Energy may be provided by an implanted battery that may be capable of wireless recharge, thereby enabling long-term use. Finally, the system may be intended for temporary monitoring followed by surgical removal or for quasi-permanent use such as that supported by pace-makers and implantable defibrillators.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, hardware processor, computer processor, central processing unit (CPU), and computer are used synonymously to denote a device capable of executing the instructions and communicating with input/output interfaces and/or peripheral devices, and that the terms processor, hardware processor, computer processor, CPU, and computer are intended to encompass single or multiple devices, single core and multicore devices, and variations thereof.

From the description herein, it will be appreciated that the present disclosure encompasses multiple embodiments which include, but are not limited to, the following:

1. An apparatus for monitoring cardiac function, the apparatus comprising: (a) a plurality of Integrated Cardio Respiratory (ICR) acoustic sensors configured to be positioned on the chest of a patient; (b) a processor coupled to the plurality of ICR acoustic sensors; and (c) a non-transitory memory storing instructions executable by the processor; (d) wherein said instructions, when executed by the processor, perform steps comprising: (i) receiving a phono-cardiogram (PCG) acoustic signal from the plurality of ICR acoustic sensors; (ii) segmenting the PCG acoustic signal to locate one or more cardiac events in the PCG acoustic signal; (iii) extracting one or more of temporal and amplitude characteristics from the PCG acoustic signal; (iv) classifying the extracted characteristics into one or more subgroups; and (v) computing ejection fraction (EF) based on the classified characteristics.

2. The apparatus or method of any preceding or following embodiment, wherein segmenting the PCG acoustic signal comprises: detecting heart sounds within the PCG acoustic signal; identifying the heart sounds based on predefined criteria; labeling heart sounds as S1 and S2 based on an interval between successive events; and decomposing the PCG signal into individual cardiac cycles.

3. The apparatus or method of any preceding or following embodiment, further comprising: (e) a plurality of ECG sensors configured to be positioned on the chest of a patient and coupled to the processor; (f) wherein said instructions, when executed by the processor, further perform steps comprising: (i) receiving an ECG sensor signal from the plurality of ECG sensors; (ii) processing the ECG sensor signal to calculate an R wave onset in the ECG sensor signal; (iii) wherein the R wave onset is used enable timing and identification of PCG acoustic signatures within the cardiac cycle.

4. The apparatus or method of any preceding or following embodiment, wherein identification of PCG acoustic signatures comprises identification of S1 and S2 events within the cardiac cycle.

5. The apparatus or method of any preceding or following embodiment, wherein the extracted temporal characteristics comprise one or more of: electromechanical activation time (EMAT), total electromechanical systolic interval ($QS_2$), S1 duration, S2 duration, mitral cessation-to-opening time (MCOT), left ventricular ejection time (LVET), and left-ventricular systolic time (LVST).

6. The apparatus or method of any preceding or following embodiment: wherein the PCG signal is analyzed in within an envelope segment containing two consecutive cardiac cycles; and wherein the extracted amplitude characteristics comprise one or more of: the root-mean-square (RMS) of the PCG signal envelope segment normalized by RMS of the PCG signal of the entire cardiac cycle; the peak amplitude of the PCG signal segment, normalized by variance of the PCG signal of the entire cardiac cycle; and the peak amplitude of envelope segment, normalized by the envelope mean value for the entire cardiac cycle.

7. The apparatus or method of any preceding or following embodiment, further comprising: extracting one or more frequency characteristics from the PCG signal by performing Phonocardiogram Carrier Signal Analysis (PCSA).

8. The apparatus or method of any preceding or following embodiment, wherein PCSA comprises AM-FM decomposition of S1 and S2 events within the PCG signal to yield a carrier signal with unit amplitude.

9. The apparatus or method of any preceding or following embodiment, wherein processing the ECG sensor signal to calculate an R wave onset in the signal comprises: (a) band-pass filtering the ECG sensor signal; (b) multiplying the filtered signal by its derivative; (c) computing an envelope of the multiplied signal; (d) identifying R waves in the computed envelope; (e) identifying corresponding peaks in the filtered signal; and (f) determining an R wave onset in filtered signal.

10. The apparatus or method of any preceding or following embodiment, wherein classifying the extracted characteristics comprises applying a Neural Network (NN) across a plurality of patients to generate a global classifier, and assigning patients to a set of subgroups based on a computed EF value, where each such subgroup has its own NN sub-classifier.

11. The apparatus or method of any preceding or following embodiment, wherein the plurality of ICR acoustic sensors disposed within an ICR sensor support configured to support the ICR acoustic sensors on the patient at locations based on typical auscultatory sites.

12. The apparatus of claim 1, wherein the instructions are further configured for: preprocessing the PCG acoustic signal using Short-Time Spectral Amplitude Log Minimum Mean Square Error (STSA-log-MMSE) noise suppression; wherein timing of the cardiac cycle based the acquired R wave onset is used to determine regions of acoustic inactivity as an input to STSA-log-MMSE.

13. A method for monitoring cardiac function, the method comprising: receiving a phonocardiogram (PCG) acoustic signal from the plurality of ICR acoustic sensors positioned on the chest of a patient; segmenting the PCG acoustic signal to locate one or more cardiac events in the PCG acoustic signal; extracting one or more of temporal and amplitude characteristics from the PCG acoustic signal; classifying the extracted characteristics into one or more subgroups; computing ejection fraction (EF) based on the classified characteristics; and outputting the computed EF for display; wherein said method is performed by a processor executing instructions stored on a non-transitory memory.

14. The apparatus or method of any preceding or following embodiment, wherein segmenting the PCG acoustic signal comprises: detecting heart sounds within the PCG acoustic signal; identifying the heart sounds based on predefined criteria; labeling heart sounds as S1 and S2 based on an interval between successive events; and decomposing the PCG signal into individual cardiac cycles.

15. The apparatus or method of any preceding or following embodiment, further comprising: receiving an ECG sensor signal, concurrently with reception of the PCG acoustic signal, from the plurality of ECG sensors positioned on the chest of the patient processing the ECG sensor signal to calculate an R wave onset in the ECG sensor signal; and wherein the R wave onset is used enable timing and identification of PCG acoustic signatures within the cardiac cycle.

16. The apparatus or method of any preceding or following embodiment, wherein identification of PCG acoustic signatures comprises identification of S1 and S2 events within the cardiac cycle.

17. The apparatus or method of any preceding or following embodiment, wherein the extracted temporal characteristics comprise one or more of: electromechanical activation time (EMAT), total electromechanical systolic interval ($QS_2$), S1 duration, S2 duration, mitral cessation-to-opening time (MCOT), left ventricular ejection time (LVET), and left-ventricular systolic time (LVST).

18. The apparatus or method of any preceding or following embodiment: wherein the PCG signal is analyzed in within an envelope segment containing two consecutive cardiac cycles; and wherein the extracted amplitude characteristics comprise one or more of: the root-mean-square (RMS) of the PCG signal envelope segment normalized by RMS of the PCG signal of the entire cardiac cycle; the peak amplitude of the PCG signal segment, normalized by variance of the PCG signal of the entire cardiac cycle; and the peak amplitude of envelope segment, normalized by the envelope mean value for the entire cardiac cycle.

19. The apparatus or method of any preceding or following embodiment, further comprising: extracting one or more frequency characteristics from the PCG signal by performing Phonocardiogram Carrier Signal Analysis (PCSA).

20. The apparatus or method of any preceding or following embodiment, wherein PCSA comprises AM-FM decomposition of S1 and S2 events within the PCG signal to yield a carrier signal with unit amplitude.

21. The apparatus or method of any preceding or following embodiment, wherein processing the ECG sensor signal to calculate an R wave onset in the signal comprises: band-pass filtering the ECG sensor signal; multiplying the filtered signal by its derivative; computing an envelope of the multiplied signal; identifying R waves in the computed envelope; identifying corresponding peaks in the filtered signal; and determining an R wave onset in filtered signal.

22. The apparatus or method of any preceding or following embodiment, wherein classifying the extracted characteristics comprises applying a Neural Network (NN) across a plurality of patients to generate a global classifier, and assigning patients to a set of subgroups based on a computed EF value, where each such subgroup has its own NN sub-classifier.

23. The apparatus or method of any preceding or following embodiment, wherein the instructions are further configured for: preprocessing the PCG acoustic signal using Short-Time Spectral Amplitude Log Minimum Mean Square Error (STSA-log-MMSE) noise suppression; wherein timing of the cardiac cycle based the acquired R wave onset is used to determine regions of acoustic inactivity as an input to STSA-log-MMSE.

24. An apparatus for monitoring cardiac function, the apparatus comprising: (a) a plurality of ECG sensors configured to be positioned on the chest of a patient; (b) a plurality of Integrated Cardio Respiratory (ICR) acoustic sensors configured to be positioned on the chest of a patient; (c) a processor coupled to the plurality of ECG sensors and ICR acoustic sensors; and (d) a non-transitory memory storing instructions executable by the processor; (e) wherein said instructions, when executed by the processor, perform steps comprising: (i) receiving a signal from the plurality of ECG sensors; (ii) processing the ECG sensor signal to calculate an R wave onset in the signal; (iii) receiving a phonocardiogram (PCG) acoustic signal from the ICR acoustic sensors; (iv) processing the PCG acoustic signal to locate one or more cardiac events in the PCG acoustic signal; and (v) extracting one or more temporal and amplitude (TA) characteristics from the PCG acoustic signal.

25. The apparatus or method of any preceding or following embodiment, wherein the one or more temporal and amplitude (TA) characteristics comprise one or more of: electromechanical activation time (EMAT), total electromechanical systolic interval ($QS_2$), S1 duration, S2 duration, mitral cessation-to-opening time (MCOT), left ventricular ejection time (LVET), and left-ventricular systolic time (LVST).

26. The apparatus or method of any preceding or following embodiment, wherein processing the ECG sensor signal to calculate an R wave onset in the signal comprises: (a) band-pass filtering the ECG sensor signal; (b) multiplying the filtered signal by its derivative; (c) computing an envelope of the multiplied signal; (d) identifying R waves in the computed envelope; (e) identifying corresponding peaks in the filtered signal; and (f) determining an R wave onset in filtered signal.

27. A method for monitoring cardiac function, the method comprising: (a) receiving a signal from a plurality of ECG sensors; (b) processing the ECG sensor signal to calculate an R wave onset in the signal; (c) receiving a phonocardiogram (PCG) acoustic signal from a plurality of ICR acoustic sensors; (d) processing the PCG acoustic signal to locate one or more cardiac events in the PCG acoustic signal; and (e) extracting one or more temporal and amplitude (TA) characteristics from the PCG acoustic signal; (f) wherein said method is performed by a processor executing instructions stored on a non-transitory memory.

28. The apparatus or method of any preceding or following embodiment, wherein the one or more temporal and amplitude (TA) characteristics comprise one or more of: electromechanical activation time (EMAT), total electromechanical systolic interval ($QS_2$), S1 duration, S2 duration, mitral cessation-to-opening time (MCOT), left ventricular ejection time (LVET), and left-ventricular systolic time (LVST).

29. The apparatus or method of any preceding or following embodiment, wherein processing the ECG sensor signal to calculate an R wave onset in the signal comprises: (a) band-pass filtering the ECG sensor signal; (b) multiplying the filtered signal by its derivative; (c) computing an envelope of the multiplied signal; (d) identifying R waves in the computed envelope; (e) identifying corresponding peaks in the filtered signal; and (f) determining an R wave onset in filtered signal.

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

Sensor Application System Size Ranges According To Patient Height

| ICR Sensor Application System Size | Patient Height (inches) | Patient Height (cm) |
| --- | --- | --- |
| X-Small | (less than 66) | (less than 168) |
| Small | (66-68) | (168-173) |
| Medium | (68-71) | (173-180) |
| Large | (71-74) | (180-188) |
| X_Large | (greater than 74) | (greater than 188) |

What is claimed is:

1. An apparatus for monitoring cardiac function, the apparatus comprising:
   (a) a plurality of Integrated Cardio Respiratory (ICR) acoustic sensors configured to be positioned on the chest of a patient;
   (b) a processor coupled to the plurality of ICR acoustic sensors; and
   (c) a non-transitory memory storing instructions executable by the processor;
   (d) wherein said instructions, when executed by the processor, perform steps comprising:
      (i) receiving a phonocardiogram (PCG) acoustic signal from the plurality of ICR acoustic sensors;
      (ii) segmenting the PCG acoustic signal to locate one or more cardiac events in the PCG acoustic signal;
      (iii) extracting one or more of temporal and amplitude characteristics from the PCG acoustic signal;
      (iv) classifying the extracted characteristics into one or more subgroups with a classifier; and
      (v) computing ejection fraction (EF) based on the classified characteristics.

2. The apparatus of claim 1, wherein segmenting the PCG acoustic signal comprises:
   detecting heart sounds within the PCG acoustic signal;
   identifying the heart sounds based on predefined criteria;
   labeling heart sounds as S1 and S2 based on an interval between successive events; and
   decomposing the PCG signal into individual cardiac cycles.

3. The apparatus of claim 1, further comprising:
   (e) a plurality of ECG sensors configured to be positioned on the chest of a patient and coupled to the processor;

(f) wherein said instructions, when executed by the processor, further perform steps comprising:
  (i) receiving an ECG sensor signal from the plurality of ECG sensors;
  (ii) processing the ECG sensor signal to calculate an R wave onset in the ECG sensor signal;
  (iii) wherein the R wave onset is used enable timing and identification of PCG acoustic signatures within the cardiac cycle.

4. The apparatus of claim 3, wherein identification of PCG acoustic signatures comprises identification of S1 and S2 events within the cardiac cycle.

5. The apparatus of claim 4, wherein the extracted temporal characteristics comprise one or more of:
  electromechanical activation time (EMAT), total electromechanical systolic interval ($QS_2$), S1 duration, S2 duration, mitral cessation-to-opening time (MCOT), left ventricular ejection time (LVET), and left-ventricular systolic time (LVST).

6. The apparatus of claim 4:
  wherein the PCG signal is analyzed in within an envelope segment containing two consecutive cardiac cycles; and
  wherein the extracted amplitude characteristics comprise one or more of: the root-mean-square (RMS) of the PCG signal envelope segment normalized by RMS of the PCG signal of the entire cardiac cycle; the peak amplitude of the PCG signal segment, normalized by variance of the PCG signal of the entire cardiac cycle; and the peak amplitude of envelope segment, normalized by the envelope mean value for the entire cardiac cycle.

7. The apparatus of claim 3, wherein processing the ECG sensor signal to calculate an R wave onset in the signal comprises:
  (a) band-pass filtering the ECG sensor signal;
  (b) multiplying the filtered signal by its derivative;
  (c) computing an envelope of the multiplied signal;
  (d) identifying R waves in the computed envelope;
  (e) identifying corresponding peaks in the filtered signal; and
  (f) determining an R wave onset in filtered signal.

8. The apparatus of claim 1, further comprising:
  extracting one or more frequency characteristics from the PCG signal by performing Phonocardiogram Carrier Signal Analysis (PCSA).

9. The apparatus of claim 8, wherein PCSA comprises AM-FM decomposition of S1 and S2 events within the PCG signal to yield a carrier signal with unit amplitude.

10. The apparatus of claim 1, wherein classifying the extracted characteristics comprises applying a Neural Network (NN) across a plurality of patients to generate a global classifier, and assigning patients to a set of subgroups based on a computed EF value, where each such subgroup has its own NN sub-classifier.

11. The apparatus of claim 1, wherein the plurality of ICR acoustic sensors disposed within an ICR sensor support configured to support the ICR acoustic sensors on the patient at locations based on typical auscultatory sites.

12. The apparatus of claim 1, wherein the instructions are further configured for:
  preprocessing the PCG acoustic signal using Short-Time Spectral Amplitude Log Minimum Mean Square Error (STSA-log-MMSE) noise suppression;
  wherein timing of the cardiac cycle based the acquired R wave onset is used to determine regions of acoustic inactivity as an input to STSA-log-MMSE.

13. A method for monitoring cardiac function, the method comprising:
  receiving a phonocardiogram (PCG) acoustic signal from the plurality of ICR acoustic sensors positioned on the chest of a patient;
  segmenting the PCG acoustic signal to locate one or more cardiac events in the PCG acoustic signal;
  extracting one or more of temporal and amplitude characteristics from the PCG acoustic signal;
  classifying the extracted characteristics into one or more subgroups;
  computing ejection fraction (EF) based on the classified characteristics; and
  outputting the computed EF for display;
  wherein said method is performed by a processor executing instructions stored on a non-transitory memory.

14. The method of claim 13, wherein segmenting the PCG acoustic signal comprises:
  detecting heart sounds within the PCG acoustic signal;
  identifying the heart sounds based on predefined criteria;
  labeling heart sounds as S1 and S2 based on an interval between successive events; and
  decomposing the PCG signal into individual cardiac cycles.

15. The method of claim 13, further comprising:
  receiving an ECG sensor signal, concurrently with reception of the PCG acoustic signal, from the plurality of ECG sensors positioned on the chest of the patient
  processing the ECG sensor signal to calculate an R wave onset in the ECG sensor signal; and
  wherein the R wave onset is used enable timing and identification of PCG acoustic signatures within the cardiac cycle.

16. The method of claim 15, wherein identification of PCG acoustic signatures comprises identification of S1 and S2 events within the cardiac cycle.

17. The method of claim 16, wherein the extracted temporal characteristics comprise one or more of:
  electromechanical activation time (EMAT), total electromechanical systolic interval ($QS_2$), S1 duration, S2 duration, mitral cessation-to-opening time (MCOT), left ventricular ejection time (LVET), and left-ventricular systolic time (LVST).

18. The method of claim 16:
  wherein the PCG signal is analyzed in within an envelope segment containing two consecutive cardiac cycles; and
  wherein the extracted amplitude characteristics comprise one or more of: the root-mean-square (RMS) of the PCG signal envelope segment normalized by RMS of the PCG signal of the entire cardiac cycle; the peak amplitude of the PCG signal segment, normalized by variance of the PCG signal of the entire cardiac cycle; and the peak amplitude of envelope segment, normalized by the envelope mean value for the entire cardiac cycle.

19. The method of claim 13, further comprising:
  extracting one or more frequency characteristics from the PCG signal by performing Phonocardiogram Carrier Signal Analysis (PCSA).

20. The method of claim 19, wherein PCSA comprises AM-FM decomposition of S1 and S2 events within the PCG signal to yield a carrier signal with unit amplitude.

21. The method of claim 15, wherein processing the ECG sensor signal to calculate an R wave onset in the signal comprises:
   band-pass filtering the ECG sensor signal;
   multiplying the filtered signal by its derivative;
   computing an envelope of the multiplied signal;
   identifying R waves in the computed envelope;
   identifying corresponding peaks in the filtered signal; and
   determining an R wave onset in filtered signal.

22. The method of claim 13, wherein classifying the extracted characteristics comprises applying a Neural Network (NN) across a plurality of patients to generate a global classifier, and assigning patients to a set of subgroups based on a computed EF value, where each such subgroup has its own NN sub-classifier.

23. The method of claim 13, wherein the instructions are further configured for:
   preprocessing the PCG acoustic signal using Short-Time Spectral Amplitude Log Minimum Mean Square Error (STSA-log-MMSE) noise suppression;
   wherein timing of the cardiac cycle based the acquired R wave onset is used to determine regions of acoustic inactivity as an input to STSA-log-MMSE.

* * * * *